US008423105B2

(12) United States Patent
Genoe et al.

(10) Patent No.: US 8,423,105 B2
(45) Date of Patent: Apr. 16, 2013

(54) SENSOR FOR ELIMINATING UNDESIRED COMPONENTS AND MEASUREMENTS METHOD USING SAID SENSOR

(75) Inventors: Jan Genoe, Messelbroek (BE); Paul Heremans, Leuven (BE)

(73) Assignee: IMEC, Leuven (BE)

( * ) Notice: Subject to any disclaimer, the term of this patent is extended or adjusted under 35 U.S.C. 154(b) by 1261 days.

(21) Appl. No.: 11/918,816

(22) PCT Filed: Apr. 5, 2006

(86) PCT No.: PCT/EP2006/061343
§ 371 (c)(1),
(2), (4) Date: Sep. 2, 2008

(87) PCT Pub. No.: WO2006/111472
PCT Pub. Date: Oct. 26, 2006

(65) Prior Publication Data
US 2008/0312517 A1 Dec. 18, 2008

Related U.S. Application Data

(60) Provisional application No. 60/672,568, filed on Apr. 18, 2005.

(51) Int. Cl.
*A61B 5/00* (2006.01)

(52) U.S. Cl.
USPC .......................................................... 600/323

(58) Field of Classification Search .................. 600/316, 600/323
See application file for complete search history.

(56) References Cited

U.S. PATENT DOCUMENTS

| | | | |
|---|---|---|---|
| 4,606,637 | A | 8/1986 | Geen et al. |
| 4,792,997 | A | 12/1988 | Toussaint et al. |
| 5,488,415 | A | 1/1996 | Uno et al. |
| 5,705,807 | A | 1/1998 | Throngnumchai et al. |
| 5,817,008 | A | 10/1998 | Rafert et al. |
| 5,912,463 | A | 6/1999 | Mizuno et al. |
| 6,549,795 | B1 | 4/2003 | Chance |
| 7,072,702 | B2 | 7/2006 | Edgar, Jr. et al. |
| 2004/0008270 | A1 | 1/2004 | Hisamatsu et al. |
| 2005/0051707 | A1 | 3/2005 | Bamji et al. |
| 2005/0077925 | A1 | 4/2005 | Bernardson |

FOREIGN PATENT DOCUMENTS

| | | |
|---|---|---|
| EP | 1 475 957 A1 | 11/2004 |
| EP | 1 515 541 A2 | 3/2005 |
| GB | 2 377 489 A | 1/2003 |
| WO | 02/26113 | 4/2002 |

OTHER PUBLICATIONS

Rocha et al., "CMOS X-ray Image Sensor with Pixel Level A/D Conversion," Proceedings of the 29th European Solid-State Circuits Conference (ESSCIRC 2003), Sep. 16-18, 2003, Estoril, Portugal, p. 121-124.

Taris et al., "A 0.9V body effect feedback 2 GHz Low Noise Amplifier," Proceedings of the 29th European Solid-State Circuits Conference (ESSCIRC 2003), Sep. 16-18, 2003, Estoril, Portugal, p. 659-662.

Tepegoz et al., "A Readout Circuit for QWIP Infrared Detector Arrays using Current Mirroring Integration," Proceedings of the 29th European Solid-State Circuits Conference (ESSCIRC 2003), Sep. 16-18, 2003, Estoril, Portugal, p. 133-136.

Someya et al., "A large-area, flexible pressure sensor matrix with organic field-effect transistors for artificial skin applications," Proceedings of the National Academy of Sciences (PNAS), Jul. 6, 2004, vol. 101, No. 27, p. 9966-9970.

*Primary Examiner* — Max Hindenburg
(74) *Attorney, Agent, or Firm* — McDonnell Boehnen Hulbert & Berghoff LLP

(57) ABSTRACT

In the present invention a novel method and device for measuring characteristics from a relatively weak signal comprising desired and undesired components is presented. Undesired signals may arise from the nature of the characteristic, from the detector or from the circuitry. The signal is extracted from a first measurement element (1) comprising these desired and undesired components. Using another signal from this first measurement element or from another second measurement element (2) the undesired components can be eliminated. The measurement method is extremely useful when using organic materials for the detectors, electronic circuitry, and measurement elements. These devices can be produced relatively cheap, but less reliable. They can also be combined in a one- or two-dimensional array for measuring characteristics over a larger area.

20 Claims, 9 Drawing Sheets

SENSOR FOR ELIMINATING UNDESIRED COMPONENTS AND MEASUREMENTS METHOD USING SAID SENSOR

RELATED APPLICATIONS

This application claims priority under 35 U.S.C. §§119 and 365 of International Patent Application Number PCT/EP2006/061343 filed Apr. 5, 2006 which claims priority under 35 U.S.C. §§120 and 365 of U.S. Provisional Patent Application No. 60/672,568, filed Apr. 18, 2005, both of which are incorporated herein by reference.

TECHNICAL FIELD

This invention relates to the field of electronic circuitry for eliminating undesired components from a measurement signal.

BACKGROUND

Circuitry and detectors for imaging are known in the art (J. G. Rocha et al in Proceedings of the 29$^{th}$ European Solid-State Circuits Conference (ESSCIRC 2003), 16-18 Sep. 2003, Estoril, Portugal, p 121-124, Thierry Taris et al in Proceedings of the 29$^{th}$ European Solid-State Circuits Conference (ESSCIRC 2003), 16-18 Sep. 2003, Estoril, Portugal, p 659-662, Murat Tepegoz et al in Proceedings of the 29$^{th}$ European Solid-State Circuits Conference (ESSCIRC 2003), 16-18 Sep. 2003, Estoril, Portugal, p 133-136, Takao Someya et al in Proceedings of the National Academy of Sciences (PNAS), Jul. 6, 2004, Vol. 101, No 27, p 9966-9970). Also a method for removing motional artefacts from devices sensing parameters of the body is disclosed in US2005 0033129. An apparatus for determining pulse oximetry is disclosed in WO02 26113. A conformal pulse oximetry sensor and monitor are disclosed in U.S. Pat. No. 5,817,008.

SUMMARY

It is an aim of the present disclosure to provide a method and device for measuring characteristics from a relatively weak signal comprising desired and undesired components.

Particular and preferred aspects of the invention can be found in the independent and dependent claims. Features from the dependent claims may be combined with features of the independent claims and with features of other dependent claims.

A sensor is described comprising at least one sensor unit. A combination of sensor units can be arranged according to a certain geometrical organisation. Each sensor unit comprises:
A charge storage element.
A first circuitry part connected to the charge storage element and to a first measurement element. This measurement element records a measurement signal. The first circuitry part transforms the measurement signal into a first measurement current (indicative of a first measurement value recorded by the measurement element). This measurement current comprises one or more desired components and one or more undesired components. This first circuitry part, comprising a first switching element, periodically applies this first measurement current to the charge storage element such that the charge storage element is charged.
A second circuitry part connected to the charge storage element and either to the first measurement element or a second measurement element. This measurement element records a measurement signal. This second circuitry part transforms the measurement signal into a second measurement current (indicative of a second measurement value), consisting of the undesired components. This second circuitry part, comprising a second switching element, periodically applies the second measurement current to the charge storage element. That way the charge storage element is discharged.
The first and second switching elements can be switched between a conducting state and a non-conducting state.
Control circuitry for applying voltages to the first and second switching elements according to a predetermined periodical timing scheme. In each period of this timing scheme the first and second switching elements are switched to the conducting state for a given time such that charge stored on the charge storage element as a result of the undesired components of the first measurement current is substantially equal to the charge which is removed from the charge storage element as a result of the second measurement current.

This sensor makes it possible to measure characteristics of a relatively weak signal comprising desired and undesired components. Undesired components are eliminated and the signal strength is increased. Undesired and weak signals may arise from the nature of the characteristic, from the detector or from the circuitry. The measurement method is extremely useful when using detectors, electronic circuitry, and measurement elements, which are less reliable, but often cheaper.

In an embodiment the first and second circuitry parts are current sources arranged as a current mirror. That way charge is stored on the charge storage device by the first measurement current and charge is removed from the charge storage device by the second current measurement current at the same rate.

In another embodiment, each sensor unit further comprises a third circuitry part connecting the charge storage element with an output. This third circuitry part is designed to conduct charge accumulated on the charge storage element to the output after a predefined number of periods using a third switching element. The third circuitry part is also designed to apply voltages to the third switching element after this predefined number of said periods. This allows the accumulation of charge on the charge storage element, whereby the strength of the signal which is periodically fed to the output is increased with respect to the measurement signal.

In another embodiment, the switching elements have an uncertain threshold voltage that may vary within a predefined voltage range. Each sensor unit further comprises control circuitry for applying voltages to these switching elements outside this predefined voltage range, so that the switching elements are switched between a conducting state and a non-conducting state or between an on and off state on opposite sides of this predefined voltage range. That way the voltage range in which the threshold voltage is uncertain can be avoided and linear operation of the switching elements can be ensured.

In an embodiment, the sensor is designed for treatment of periodic measurement signals, which continuously vary between a maximum and a minimum. Here, the predetermined timing scheme is determined such that the first measurement value is around the maximum of the periodic signal and the second measurement value is around the minimum of the periodic measurement signal. In this way, the first measurement current which is conducted to the charge storage element represents the maximum of the periodic signal and the second measurement current which is conducted to the charge storage element represents the minimum of the periodic measurement signal. This approach is for example useful when the desired component has a periodic behaviour and the undesired components produce a constant measurement value. Therefore, the control circuitry part preferably further comprises a control logic block to determine the occurrence of the maximum and the minimum of this periodic measurement signal.

In an embodiment the first measurement element comprises at least one light detector. This is used in case the characteristic is measured by means of light. In another embodiment the first measurement element comprises a light detector and the second measurement element comprises a blind detector. A blind detector is a light detector being screened or covered from incident light. This setup, using a blind detector, allows eliminating dark current present in various light detectors.

In another embodiment, each sensor unit further comprises at least one light emitting diode for illuminating the measurement elements, for example by reflection on human tissue. With a light emitting diode as light source, the intensity of reflected light can be increased. A light emitting diode can also be used in case the intensity of other present light is unreliable.

In some applications the signal strength at two different optical wavelengths is measured to derive certain characteristics. Therefore in another embodiment each sensor unit comprises a light emitting diode with broad emission spectrum and two light detectors with narrow absorption spectrum. The absorption spectra of the two light detectors are different and fall within the broad emission spectrum of the light emitting diode.

In another embodiment the sensor unit further comprises a light-absorbing or light-reflecting layer between the light emitting diode(s) and the light detector(s). This avoids that light, coming from the light emitting diode, reaches the light detector before having penetrated the material under study.

In another embodiment the sensor units are arranged in a one or two dimensional matrix. This allows measuring characteristics over a larger area. In another embodiment, the sensor further comprises at least one connector for power and signals. In another embodiment the sensor further comprises read-out electronics for reading out said sensors in a sequential manner. In another embodiment the sensor further comprises a display, on which the read-out electronics realises a one or two-dimensional image of the charges on said charge storage elements on the different sensor units.

In another embodiment the circuitry parts, charge storage element, detector(s), and light emitting diode(s) are made of organic materials. The use of organic materials reduces production costs but can result in less reliable devices, a problem alleviated when using the measurement approach described herein.

In another embodiment the sensor is embedded in a flexible material. In another embodiment this flexible material is a bandage for covering a wound. In another embodiment this flexible material is a foil incorporated in a bandage for covering a wound. In another embodiment the foil is composed of different foils: a first foil comprising organic light emitting diode(s), a second foil comprising organic light detector(s), and a third foil comprising first, second and third circuitry elements.

In another embodiment, a method for removing one or more undesired components from a measurement signal related to a characteristic is presented. The method comprises the following steps:
  a) A first measurement value of a measurement signal is measured by a first measurement element. The output is a first measurement current, comprising one or more desired components and one or more undesired components.
  b) This first measurement current is applied to a charge storage element for a given amount of time by means of a first switching element, thereby charging this charge storage element.
  c) A second measurement value of the measurement signal is measured by this first measurement element or by a second measurement element for obtaining a second measurement current consisting of the one or more undesired components.
  d) This second measurement current is applied to the charge storage element for a given amount of time by means of a second switching element, thereby discharging the charge storage element. The charging and discharging times are chosen such that the charge stored on the charge storage element as a result of the undesired components of the first measurement current is substantially equal to the charge removed from said charge storage element as a result of the second measurement current.
  e) a) to d) are repeated a predefined number of times,
  f) Charge accumulated on the charge storage element is conducted to an output by a third switching element.

The method above allows measuring characteristics from a relatively weak signal comprising desired and undesired components. Undesired components are eliminated by applying the second measurement current to the charge storage element and the signal strength is increased by repeating steps a) to e). Undesired and weak signals may arise from the nature of the characteristic, from the detector or from the circuitry. The measurement method is extremely useful when using less reliable, but generally much cheaper, detectors, electronic circuitry, and measurement elements.

In another embodiment of the second aspect, these first, second, and third switching elements have an uncertain threshold voltage. The threshold voltage can vary within a predefined voltage range. These switching elements can be switched between a conducting state and a non-conducting state at voltages located on opposite sides of this predetermined voltage range. The method further comprising controlling the voltage applied to these switching elements outside this predetermined voltage range. That way the voltage range, in which the threshold voltage is uncertain, is avoided.

In another embodiment the measurement signal is a periodic signal. In another embodiment the first measurement current is applied to the charge storage element around the maximum of this periodic signal and the second measurement around the minimum of this periodic signal. This approach is useful when the desired component has a periodic behaviour and the undesired components produce a constant measurement value.

In another embodiment light is detected by a first light detector and the output of the light detector is a measurement current comprising one or more desired components and one or more undesired components. At other moments light is detected by this first light detector or by a second light detector, this first or second light detector outputting a second measurement current comprising these one or more undesired components only. In another embodiment this second light detector is a blind detector. A blind detector is a light detector covered from incident light. Using a blind detector, allows eliminating dark current present in various light detectors.

In another embodiment the method further comprises illuminating the material of which the characteristic is to be defined by means of at least one light emitting diode. With a light emitting diode as light source, the intensity of reflected light can be increased. A light emitting diode can also be used in case the intensity of other present light is unreliable. In another embodiment the material is illuminated with one light emitting diode with a broad emission spectrum and light is detected by a first and a second light detector with respectively a first narrow absorption spectrum and a second narrow absorption spectrum. The first light detector creates a first measurement current comprising one or more desired components and one or more undesired components. The second light detector creates a second measurement current comprising these one or more undesired components. The first and second narrow absorption spectra of the first and second light detectors are different. The first and second narrow absorption spectra of the first and second light detectors are within the broad emission spectrum of the light emitting diode. In some applications the signal strength at two different optical wavelengths is measured to derive certain characteristics.

In another embodiment the different steps represented above are repeated on different locations in a one- or two-dimensional array. This allows measuring characteristics over a larger area. Charges, stored on the charge storage element on the different locations, are conducted to an output in a sequential manner and these charges are displayed as a one- or two-dimensional image.

In another embodiment the characteristic that is to be measured is blood flow, oxygen content in blood, constituents of blood, presence of markers in blood, and concentration of markers in blood. In another embodiment the periodic signal is the heart beat cycle and the first measurement current is recorded around maximum blood pressure and the second measurement current is recorded around minimum blood pressure.

DETAILED DESCRIPTION

Figure 1:
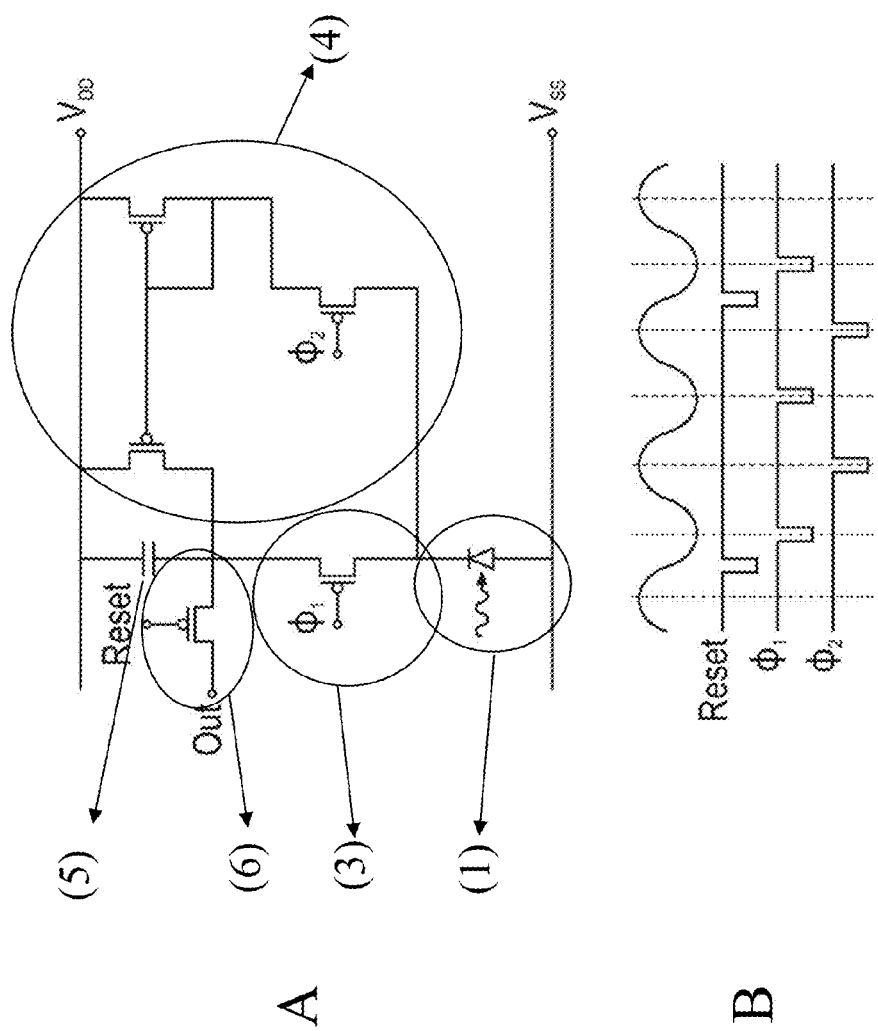
FIGS. 1A and 1B illustrate a circuit schematic and a timing diagram illustrating a control logic block and its operation when using one measurement element, in this case a light detector.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and that the embodiments of the invention described herein can operate in other orientations than described or illustrated herein.

The term "comprising", used in the claims, should not be interpreted as being restricted to the means listed thereafter; it does not exclude other elements or steps. It should be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Many measurement signals are relatively weak and contain undesired information. These undesired components should be eliminated and the signal strength should be increased. A method and a sensor are disclosed herein for measuring characteristics based on a relatively weak measurement signal showing desired and undesired components. The undesired components may be present in the signal itself, they may arise from a detector, and they may result from active circuitry or transistors within this active circuitry. The signal coming from the read-out circuitry is independent of noise or the undesired components. The method and the sensor can also make use of transistors which have an uncertain threshold voltage (VT) and are therefore unsuitable for use as signal amplifiers.

Undesired components may arise from the nature of the characteristic that is measured or from the environment in which the characteristic is measured. For example when measuring the oxygen content in the blood by the reflection of light, light is reflected by the blood and by the skin. The light reflected from the skin is preferably eliminated.

Undesired components may also arise from the measurement elements or detectors, such as light detectors, temperature sensors, humidity sensors, or biosensors. For example a light detector may show a dark current not induced by the incident light.

Undesired components can also arise from the active circuitry, for example transistors in this circuitry. These transistors may also have an uncertain VT.

Nowadays there is an increased interest in using plastic electronics for various applications as they have many advantages.

Plastic electronics can be used to integrate organic light emitting diodes (OLEDs), organic light detectors and active circuitry, such as organic transistors on flexible substrates to create composite flexible substrates and devices. Plastic electronics can be produced more easily when compared to classical electronics. If a matrix consisting of classical detectors, classical LEDS and readout electronics were used in place of organic circuit components, a very complicated pick-and-place machine could be employed to place each of the elements from the three sets on exact locations on the matrix. However, this would give rise to numerous integration issues, inherently low integration density, the danger for low integration yield, and extremely high integration costs. Thus, mass production would be extremely difficult. The advantage of using plastic electronics is the fact that components may be deposited by e.g. printing, evaporation or spin-coating and other known preferably low-cost techniques for organic electronics fabrication. These low cost technologies allow for mass production more easily than for prior art devices due to their corresponding production techniques. Moreover, relatively high integration densities can be achieved and different constituting elements can be processed in parallel, i.e. in the same process steps. This also allows for inexpensive production of one and two dimensional arrays with measurement places each having their signal generator and their signal detector and underlying electronics, providing one or two-dimensional pictures of the characteristics of the material under measurement.

Furthermore these composite devices are typically flexible and can be applied on materials having different shapes, including a human or animal body. A uniform pressure on the tissue or material can be applied, since no classical components, which are hard, are present. That way they can be for instance integrated in a bandage which covers a wound. Also making copies of bended surfaces without losing the actual dimensions would be possible.

Another advantage of using organic components to implement such an actuator (signal generator, signal provider as e.g. a light source) and signal detector (e.g. a light detector), is that such components have a different emission and/or absorption spectrum when compared to classical non-organic components. The emission and absorption spectrum of organic components can be relatively broad and their absorption spectra may be limited towards higher frequency or energy photons. This means that their emission and absorption spectra can be appropriately chosen for the specific implementation.

A disadvantage, however, of these plastic electronics is that they give rise to undesired components. Organic detectors, for example, show a significant dark current. Organic transistors may also show a poor VT control: there is a variability of the on/off threshold voltage of switching elements. The independence of the proposed measurement method of undesired components and of the characteristics of the transistors is an advantage when considering organic transistors, which typically have less reproducible properties then classical non-organic transistors. Such a measurement method allows for the use of organic material for an actuator (signal generator, signal provider as for instance a light source), a signal detector and underlying active electronics.

Figure 2:
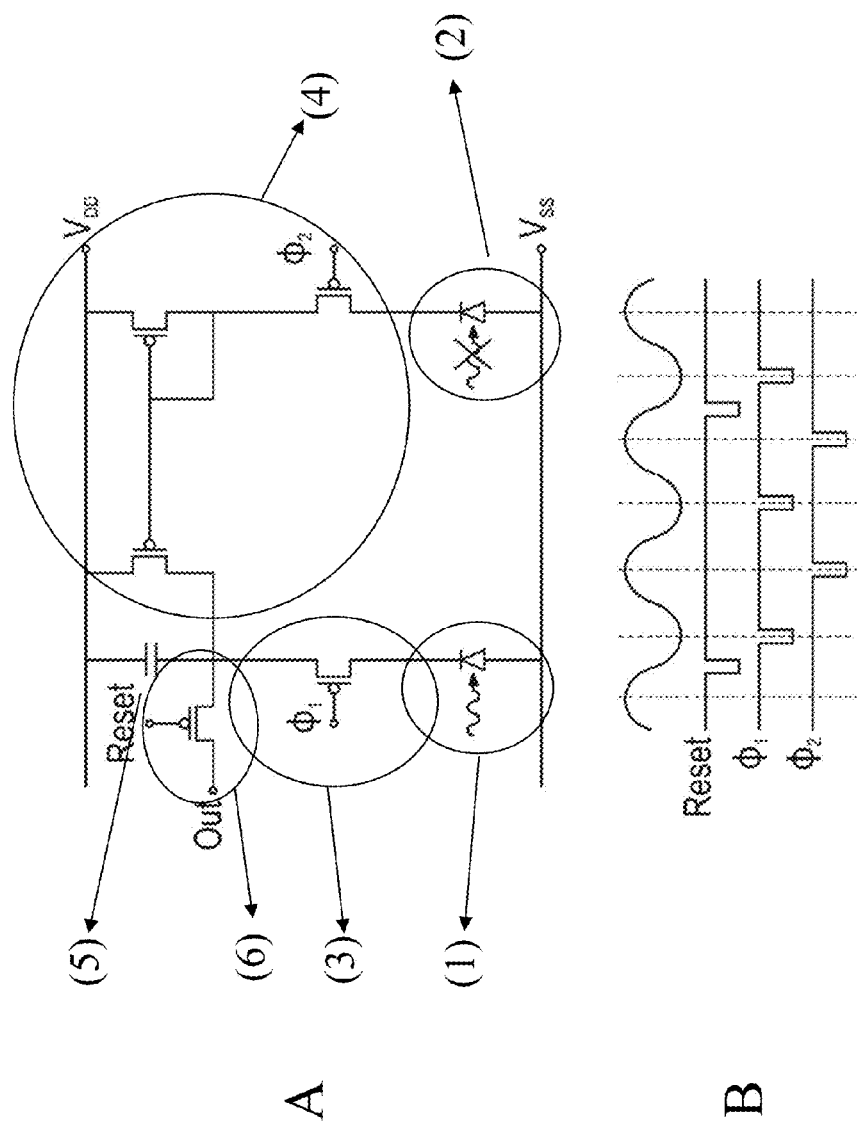
FIGS. 2A and 2B illustrate a circuit schematic and a timing diagram illustrating a control logic block and its operation when using two measurement elements, in this case a light detector in conjunction with a blind detector.

To eliminate the undesired components, a differential approach is used. This is illustrated in FIGS. 1 and 2.

A first measurement element (1) records a measurement signal. A first circuitry part (3), connected to the first measurement element transforms the measurement signal which is recorded at a given moment into a first measurement current, which is thus indicative of a first measurement value recorded at that moment. This first measurement current comprises one or more desired components and one or more undesired components. The first circuitry part (1) periodically applies this first measurement current to the charge storage element (5). That way the charge storage element is charged. This charge storage element can for example be a capacitor, but may also be any other charge storage element known to the person skilled in the art, such as for example a floating gate electrode. To be able to control this periodic charging of the charge storage element, this first circuitry part comprises a first switching element.

The same first measurement element (1) or another second measurement element (2) records a second measurement signal, i.e. records a second measurement value. A second circuitry part (4), connected to this first measurement element (FIG. 1A) or the other second measurement element (FIG. 2A) transforms the second measurement signal into a second measurement current, which is indicative of the second measurement value and consists of the undesired components. This second circuitry part (4) periodically applies the second measurement current to the charge storage element (5). Thereby the charge storage element is discharged. To be able to control the periodic discharging of the charge storage element, this second circuitry part comprises a second switching element.

The first and second circuitry parts can be current sources, arranged as a current mirror (as represented in FIGS. 1A and 2A).

Switching elements are included in the first and second circuitry parts to control the periodic charging and discharging of the charge storage element. These switching elements are switched to the conducting state by applying a voltage V, to the first switching element and by applying a voltage $V_2$ to the second switching element. Switching is done in a periodic way according to a function $\Phi_1$ for the first circuitry part and a function $\Phi_2$ for the second circuitry part (FIGS. 1A and 2A). Therefore control circuitry is included to apply these voltages to these switching elements according to a predefined periodical timing scheme (FIGS. 1B and 2B). These switching elements can be transistors. It is important that the charge stored as a result of the undesired components is substantially equal to the charge removed during discharging. In case the charging and discharging times are equal, the charging and discharging should have substantially the same charging capability.

Also other and more complicated combinations are possible to eliminate various undesired components. In FIG. 3A, the situation is represented where a first measurement element produces a first measurement current comprising desired and two sets of undesired components (a first set and a second set). This current is used to charge the charge storage element according to a function $\Phi_1$. At other moments this first measurement element produces a second measurement current consisting of the first set of undesired components. This second current is used for discharging the charge storage element, according to a function $\Phi_2$. A second measurement element produces a third measurement current comprising the second set of undesired components. This third measurement current is also used to discharge the charge storage element at certain moments in time, according to a function $\Phi_2'$.

In FIG. 4A, a first measurement element produces a first measurement current. This first measurement current comprises desired components and 2 sets of undesired components, (a) and (b). Meanwhile a second measurement element records a second measurement current, consisting of undesired components (a). The first measurement current is used for charging the charge storage element and meanwhile the second measurement current is used for discharging the charge storage element, according to a function $\Phi_1$. That way the undesired components (a) are eliminated. At other moments this first measurement element produces a third measurement current comprising only the 2 sets of undesired components (a) and (b) and the second measurement current record a fourth measurement current comprising undesired component (a). The third measurement current is used for discharging the charge storage element, thereby eliminating the undesired components (a) out of the third measurement current, and meanwhile the fourth measurement current is used for charging the charge storage element, thereby eliminating the undesired components (b) out of the first measurement current, both according to a function $\Phi_2$.

Figure 3:
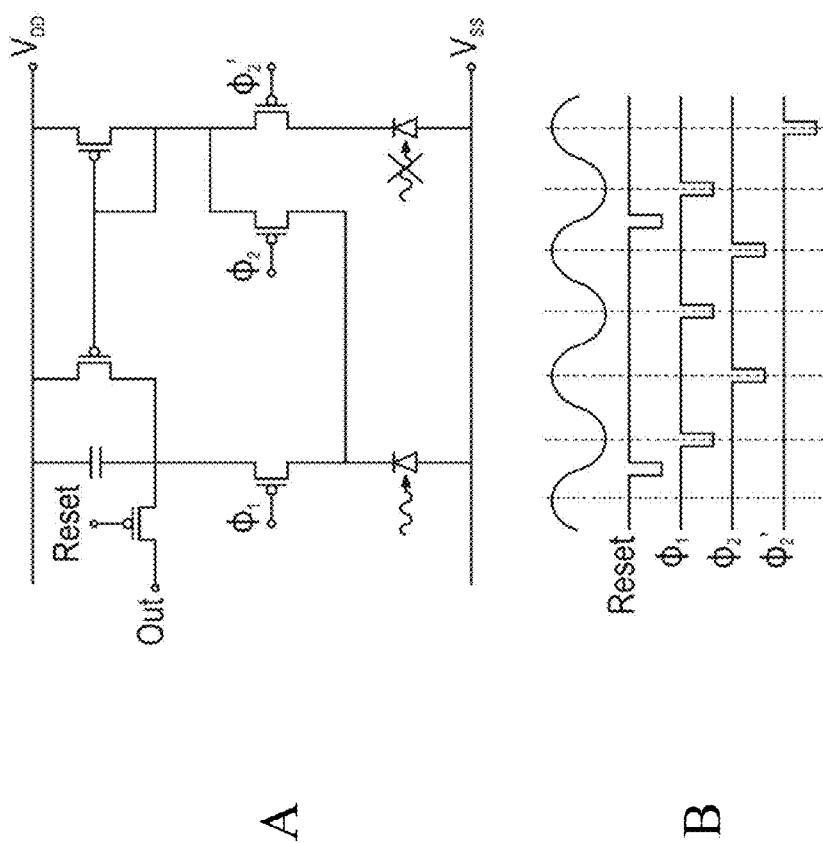
FIGS. 3A and 3B illustrate another circuit schematic and a timing diagram illustrating a control logic block and its operation when using two measurement elements, in this case a light detector in conjunction with a blind detector.
Figure 4:
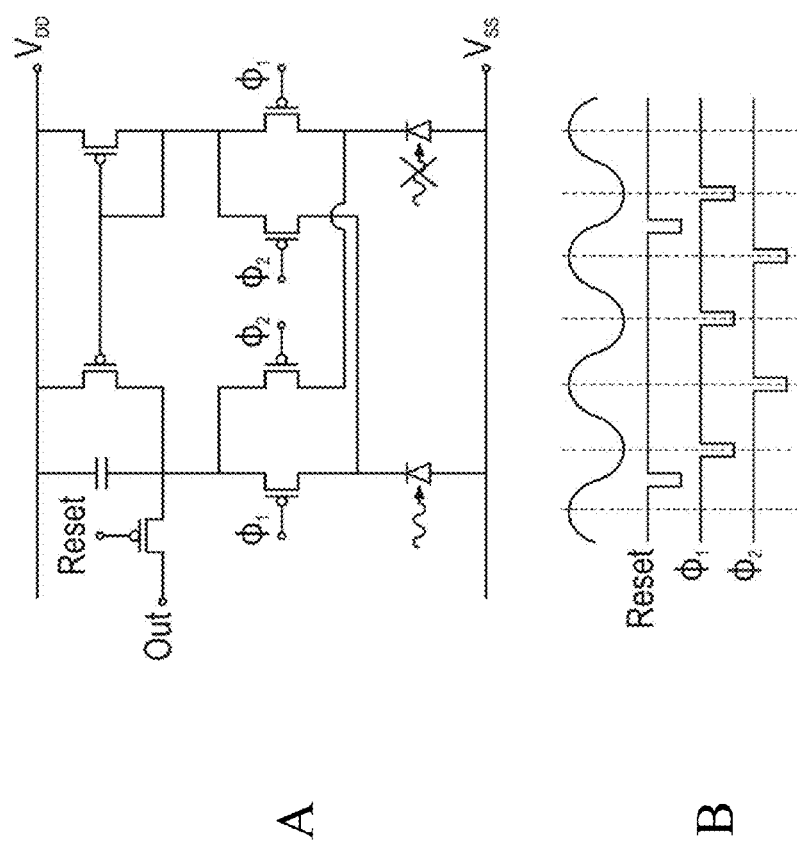
FIGS. 4A and 4B illustrate another circuit schematic and a timing diagram illustrating a control logic block and its operation when using two measurement elements, in this case a light detector in conjunction with a blind detector.

A more detailed description of a specific embodiment of FIGS. 3 and 4 is given below. In this embodiment a characteristic in blood under the skin is to be measured. The skin and underlying blood vessels can be illuminating by a light emitting diode. Reflected light is measured with a light detector. Light reflected from the blood contains information of the characteristic that is to be measured. But it comprises also undesired reflected light, e.g. light reflected from the skin and muscles. Furthermore, it also contains dark current. A current I is passing through the detector, which has 2 components;
 a current which is independent on the incoming light (dark current)
 a current which is proportional to the incoming light During the period that the clock $\phi_1$ is active ($T(\phi_1)$) the current coming from the light detector will go through the transistor which is connected with clock $\phi_1$ and will thereby reduce the voltage on the lower knot of the capacitor. The Voltage reduction equals $I(\phi_1)*T(\phi_1)/C$. $I(\phi_1)$ being the average current during the period $T(\phi_1)$.

During the period that the clock $\phi_2$ is active ($T(\phi_2)$) the current coming from the light detector will go through the transistor which is connected with clock $\phi_2$ and also through the transistor above. The latter transistor is positioned in a current-mirror configuration (e.g., the gate is in common with the neighbouring transistor). The neighbouring transistor will produce the same current, but flowing from the power supply to the capacitor (instead of the light detector), with the result that the voltage on the lower knot of the capacitor will increase. The Voltage increase equals $I(\phi_2)*T(\phi_2)/C$. $I(\phi_2)$ being the average current during the period $T(\phi_2)$.

If the length of the clocks $\phi_i$ is chosen equal, ($T(\phi_1)=T(\phi_2)= T(\phi_i)$), the voltage over the capacitor is: $[I(\phi_2)-I(\phi_1)]*T(\phi_i)/C$. This means that the voltage variation on the capacitor is:
 independent of the dark current,
 proportional to the difference in incident light flux between the flux at high pressure of the heartbeat and the flux at low pressure of the heartbeat; and
 independent of the characteristics of the transistors, if the supply voltage and the capacitor value is large enough to keep all transistors in saturation during operation, and if both transistors of the current mirror don't differ significantly.

By choosing the capacitor value large enough, one can repeat this process for a finite number of times (e.g., 1, 10, 50, 100, 1000, 10000, 100000 times) such that the eventual difference signal on the capacitor increases at every iteration and the noise signal on the capacitor become less important. Hereby a precise measurement signal can be achieved.

By means of a reset signal the voltage over the capacitor can be initially set to 0. To do this, the readout line of the memory matrix can be connected to the voltage of the power supply and subsequently the reset transistor can be activated.

For the readout of the measurement value, one can make use of the fact that the capacitor value C is chosen large, such that it is larger than the capacitor value of the read-out line. This read-out line can be precharged on the power supply voltage and made of high impedance. The opening of the reset transistor causes a charge redistribution and the voltage on the read-out line can be measured.

To measure the amount of incoming light, one can also make a single measurement (only $\phi_1$ is steered). But in such a case the dark current can be eliminated in a different way. One could make use of a blind detector, which is covered such that no light is coming in and only a dark current is measured. The difference of the measured signal in an open detector with the signal of the blind detector represents then the actually incoming light.

To summarise, the blind detector can be steered by the clock $\phi_2'$, which can be coincide with $\phi_i$ as illustrated in FIG. 4B, or shifted a little in time, as illustrated in FIG. 3B.

By choosing the charging capability of the charge storage element large enough or else by choosing the capacitor value large enough, one can repeat this process of charging and discharging for a finite number of times (e.g., 1, 10, 50, 100, 1000, 10000, 100000 times) such that the charge stored on the charge storage element or the capacitor increases at every iteration. That way an integrated value is obtained. After charging and discharging the charge storage element a number of times, the charge can be conducted to an output for analysis. That way the signal strength at the output can be increased and the noise signal on the capacitor become less important. The sets of measurement intervals can correspond with specific repetitions in for example the heartbeat cycle. In such way, an integrated value and subsequent read-out of said integrated value are achieved and the characteristic of a material, for example human or animal tissue can be determined from this integrated value.

Read-out of the charge storage element is achieved by a third circuitry part (6) connected to the charge storage element. This third circuitry part is designed to conduct charge from the charge storage element to an output of the sensor at certain moments in time, possibly in predefined time frames or in a periodic way. This can be after a number of periods of charging and discharging. To conduct the charge from the charge storage element to the output, this third circuitry part comprises a third switching element. If the switching element is in the conducting state, the charge from the charge storage element is conducted to an output. This switching element can be a transistor. The switching element can be switched to the conducting state by applying a voltage $V_3$. Periodic switching the transistor can be done according to a function called RESET in FIGS. 1 and 2.

The above differential measurement approach in combination with integration has as a further advantage that absolute values of the measurement device, which can differ over time (due to aging), are also less problematic, which is the case particularly when organic based devices are used.

In certain embodiments, such a circuit may be used for measuring the blood flow or the oxygen level of such blood flow. These circuits can also be used to generate a substantially noise free signal from an organic electronics device, which can repetitively measure a substantially invariant parameter, each measurement itself having a high-noise component.

Additionally transistors may amplify the signal difference between both measurement devices using control logic.

The switching elements can be transistors. Transistors can have an uncertain VT. VT can vary in a certain voltage range, called the uncertain voltage region, having a lower and an upper voltage. At voltages substantially above the upper voltage, the transistor is always switched to the conducting state. Below the lower voltage, the transistor is always in the non-conducting state. Transistors showing variable VT should be operated outside the region where VT varies, so voltages applied to the transistor should be outside this uncertain region. Therefore circuitry is connected to these transistors for applying voltages outside this uncertain voltage range, so that the transistors can be switched between a conducting and a non-conducting state at opposite sides of this uncertain region. The current ratio between the conducting and the non-conducting state can for example be 10, 100, or another value. In the preferred case this ratio is above 1000.

The method can be used in a device comprising a measurement device and underlying electronics that are fully integrated in an organic material, wherein the VT variability problem is often apparent.

The measurement signal may be a periodic signal. This periodicity may be present in the characteristic that is measured. An example is the measurement of a characteristic in the blood, where the heart beat cycle introduces a periodicity. Another example is a periodic gas flow in a tube. In case light reflected from the material is measured, the resulting signal will be a periodic signal.

The periodic signal may also induced by another external component. In case of detecting light reflected from a material, an external light source may be used and illumination of the material can be done in a periodic way.

In case of a periodic signal, charging of the charge storage capacitor can be done around the maximum of the periodic measurement signal and discharging can be done around the minimum of the periodic measurement signal. To detect maxima and minima in the periodic measurement signal an extra control logic block is preferably included in the control circuitry part.

Depending on the application, different combinations of first and second measurement elements and first and second circuitry parts may be possible. Possibly extra measurement elements or circuitry parts can be added or the functionality of circuitry parts can be extended. Also some other elements can be added. These measurement elements may be temperature sensors, light detectors or any other measurement means to measure a characteristic of a material. In many applications light reflected of a material gives information on the characteristic to be measured. Light reflected from the blood in the skin gives information on the oxygen content of the blood. Also, light reflected of small spots of a text or a figure gives information on the colour of this spot or text. Below several combinations of measurement elements and circuitry parts are represented. Other combinations are also possible.

For some applications one light detector, connected to the first and the second circuitry part is sufficient, as represented in FIG. 1A. The detector may first measure a signal comprising desired and undesired components. Afterwards a signal substantially comprising only undesired components is measured. The circuitry substantially eliminates the undesired components.

An example where only one light detector is needed is the measurement of blood flow under the skin. In the case of blood flow the first measurement signal is composed of light reflected by the blood and light reflected by the skin and tissue underneath the skin (at high blood pressure). The second measurement signal substantially comprises only light reflected by the skin and tissue underneath the skin (at low blood pressure). The circuitry eliminates light reflected by the skin and tissue underneath the skin.

With this circuitry and measurement method, variations of light intensity can be substantially eliminated by repeating the measurement different times before discharging the charge storage element. Also a relatively weak light intensity is not a problem as an increased signal is obtained by accumulating charge on the charge storage element over more periods.

To substantially eliminate the influence of dark current of a detector a combination of a light detector and a blind detector can be used (FIG. 2A). A blind detector is a detector which is covered to prevent incident light from entering the detector. Such a blind detector can be used for measuring dark current. This is useful in case the dark current produced by detector becomes important, for example when using organic light detectors. The method presented above can be used to substantially eliminate the dark current of the organic light detector. The first measurement current comprises the signal from the characteristic in combination with the dark current. The second measurement current, from the blind detector only, comprises the dark current.

Often an extra light source is used, such as a light emitting diode. This is useful in case the existing light intensity is insufficient or in case the light intensity is unreliable. Such a measurement device includes a mechanism for providing an optical signal on a material and a mechanism for detecting the optical signal as received after reflection from this material. In particular, the device delivering the signal may be a light emitting diode (LED) or even an organic light emitting diode (OLED). Likewise, the signal detecting device may be a photo detector or light detector, or even an organic photo detector.

Figure 5:
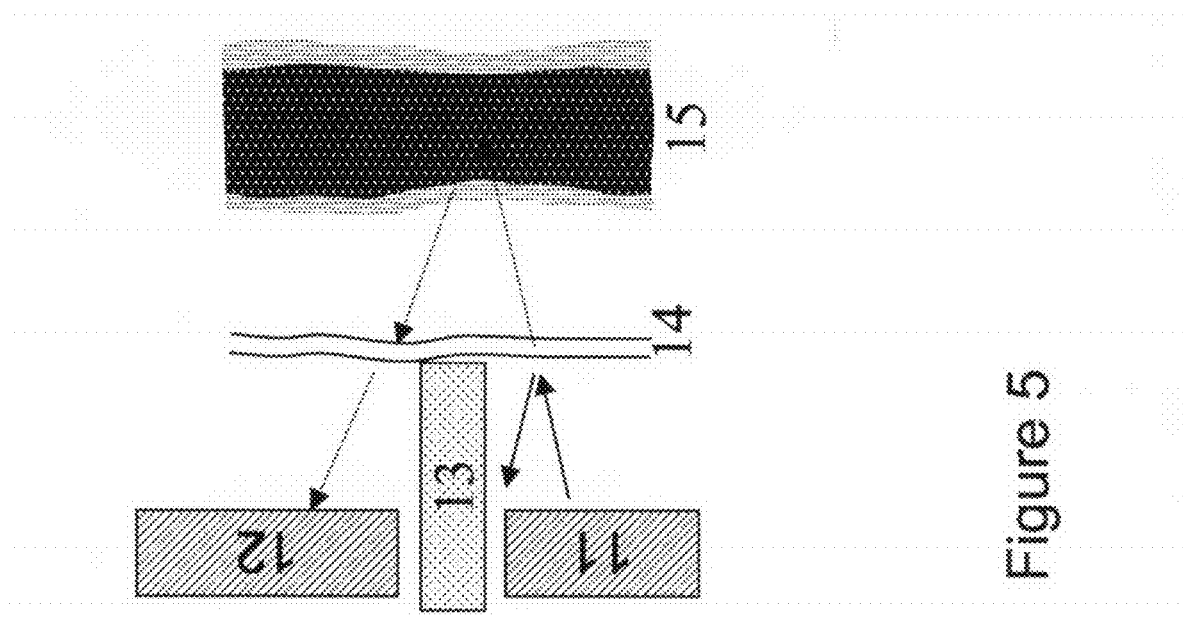
FIG. 5 illustrates basic principles of operation of a matrix of light emitting diodes (LEDs) and light detectors integrated into a bandage disposed on a patient's skin. The light emitted by the LED (11) is scattered by the blood vessel (15) and received in the detector (12). The reflected signal varies with the blood pressure and allows obtaining the blood circulation under the skin. The light reflected by the skin does not substantially vary. An absorbing or reflecting layer (13) could be placed between the LED and detector to prevent incident light that has not been scattered in the skin tissue.
Figure 6:
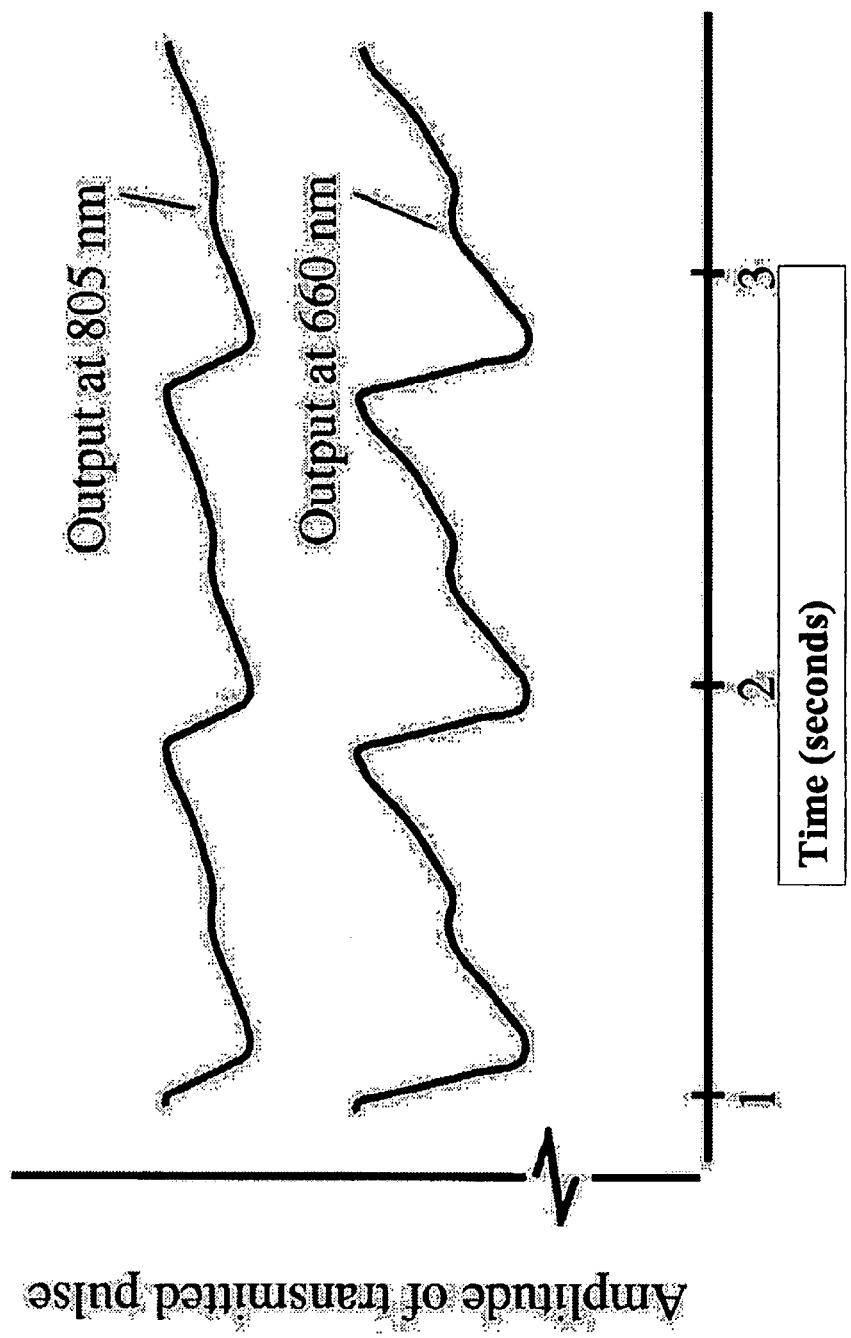
FIG. 6 illustrates measured transmission or reflection signal of the skin as a function of time, where the variation of the signal corresponds to the local blood volume variation. A similar variation is observed for different light sources (e.g. 805 nm and 660 nm), but with a different amplitude. This is related with the wavelength dependence of light scattering and absorption of blood. If only the volume variations of the blood have to be monitored, a single wavelength is sufficient. It this case the light source is preferred that results in a higher signal amplitude (e.g. 660 nm). However, if both the flow and the oxygen concentration are monitored, two signals are required (at different wavelength, for example 660 nm and 805 nm) to extract both parameters from the experimental data.

Direct illumination of the detector by the LED or by light that reflects before entering material is preferably substantially avoided. Light that has not entered the material is of no use for the detector. This is the case when the oxygen content of blood under the skin needs to be measured. This is illustrated in FIG. 5. Light emitted by the LED (11) is partially reflected by the skin (14) and partially transmitted to the blood vessel (15). Light coming from the LED (11) or reflected at the skin (14) should not reach the light detector

(12) whereas light reflected from the blood (15) should reach the detector (12). Therefore, a light-absorbing or reflecting layer (13) may be included between the LED and detector to prevent the incidence of such undesired light (can be directly incident, or indirectly incident (e.g. after reflection)) into the detector. In other words a light absorbing or reflecting structure, element or layer can be present such that the amount of light reaching the detector (originating from the light source, possibly LED) not having penetrated said material is reduced. Therefore the light absorbing or reflecting structure, element or layer can be positioned in the path of direct or indirect illumination of light generated by said emitter towards said detector. An element or layer can put in between the detector and the emitter. In a specific embodiment, such a light-absorbing layer is obtained by etching a V-groove into the substrate and filling this groove with a material that absorbs light at the wavelength being used. Alternatively, the V-groove may be filled with a metal to reflect the undesired light.

Combining light detectors and light emitting diodes (LEDs) with different wavelengths allows measurements with signals at different wavelengths. In the following, "different" is meant to indicate that the described elements have different emission or absorption spectra, e.g. they emit or absorb different frequencies. Different wavelengths can easily be obtained when the components, i.e. detectors and LEDs, are made of organic materials. Such components have a different emission and/or absorption spectrum when compared to classical non-organic components. The emission and absorption spectrum of organic components can be relatively broad and their absorption spectra may be limited towards higher frequency or energy photons. This means that their emission and absorption spectra can be appropriately chosen for the specific implementation. Different combinations of detectors and LEDs are represented below. They can easily be produced in organic materials, but in many cases also in classic non-organic materials. As an example, the measurement of the oxygen content of blood in a tissue is chosen. Different approaches are possible.

It is possible to use two LEDs with narrow emission spectra and one detector with a broad absorption spectrum. The absorption spectrum of the detector is chosen such that it can detect the wavelengths emitted by both LEDs, so that it can detect the emission spectra of both LEDs. In a situation where oxygen content of the blood is to be measured, one could put a first LED generating light at a first frequency (e.g., red light of a first freq.), a second LED generating light at a second frequency (e.g., red light of a second frequency or infrared (IR) light) and a detector, which is able to absorb both frequencies. Non-organic LEDs can emit light in a narrow frequency range. Non-organic detectors can absorb photons with energy larger then the bandgap energy, which means that if the detector is designed to collect photons of the light of a first, lower, frequency, it would also collect light at a second, higher frequency. This means that emission and detection of light of both frequencies cannot happen at the same time; as only one signal would be generated in the detector.

Organic light emitting diodes (OLED) and organic light detectors can cover only a limited frequency range or can cover a wide frequency range. Organic detectors optimized for covering both wavelengths are disclosed as well as organic detectors optimized for covering a single wavelength.

Figure 7:
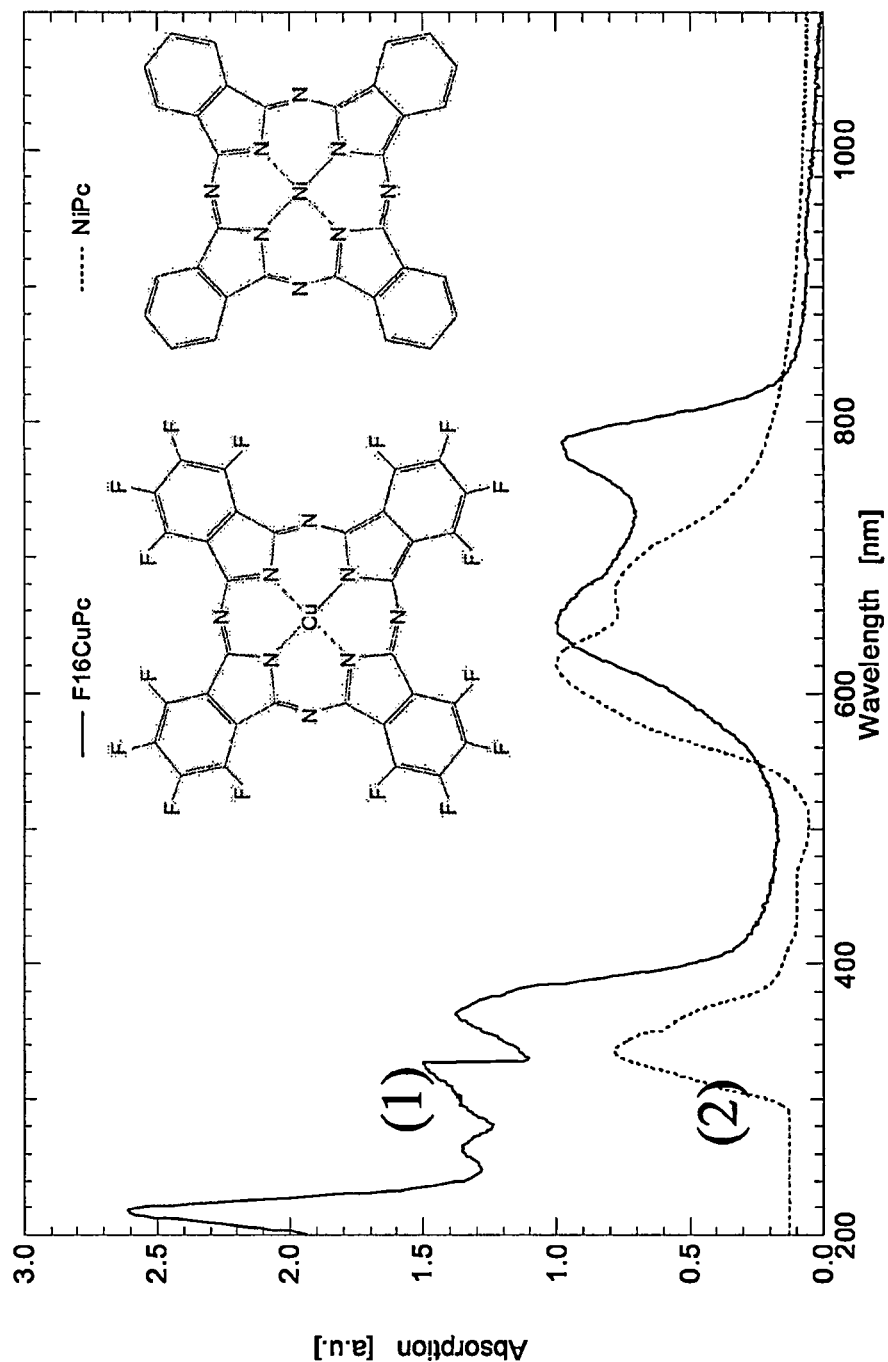
FIG. 7 illustrates absorption spectra of materials that can be used in organic detectors. The material structure, shown as an inset (e.g., F16CuPc (1) absorbs the incident light of both the red (around 600 nm) and infrared (around 800 nm) wavelengths. NiPc (2) has a high absorption of red light (around 600 nm) and a more limited absorbs ion of infrared light (around 800 nm)). The combination of detectors using both materials allows extraction of information on both blood flow and oxygen concentration.
Figure 8:
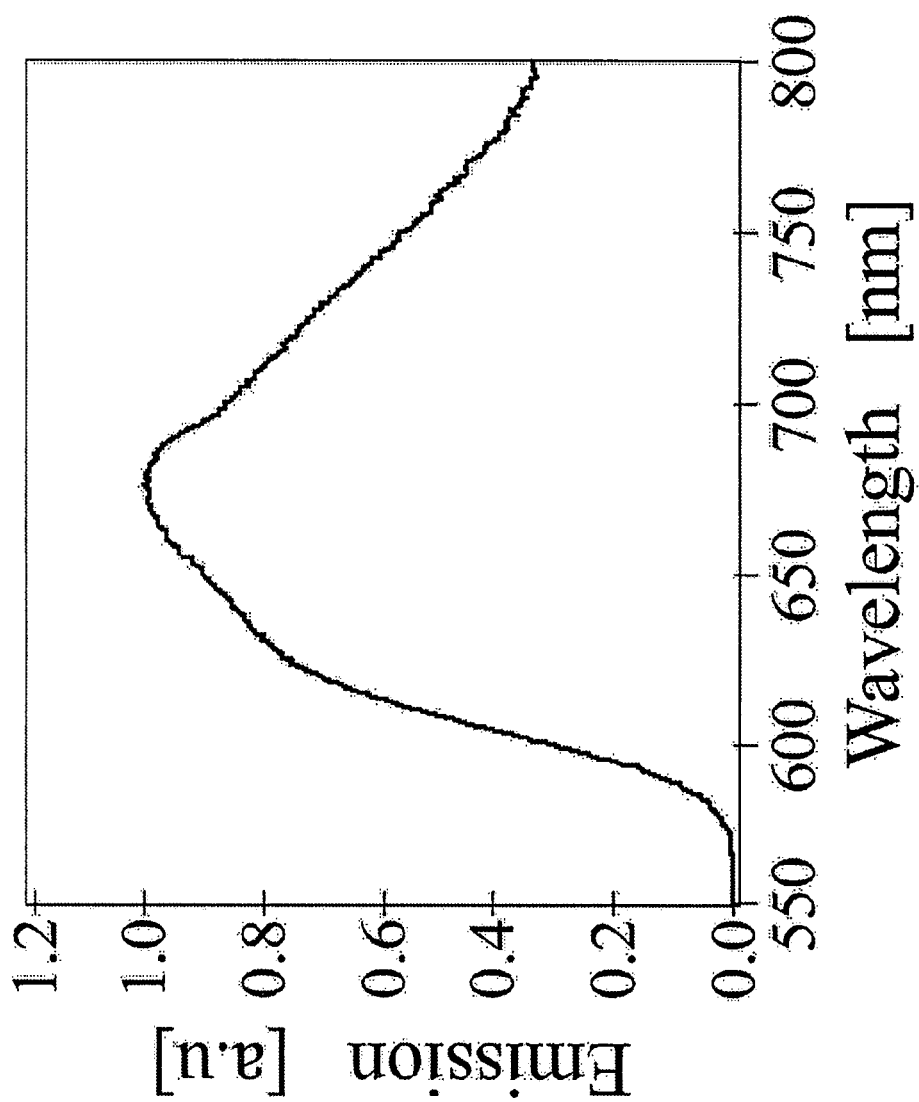
FIG. 8 is a graph illustrating an emission spectrum of the TBA[Ir(CO)(PR3)mnt)]-complex that can be used in organic LEDs, where the spectrum covers the region from red (from 600 nm) to infrared (around 800 nm).

Signals at different wavelengths can be obtained by using a signal generator (e.g., a light generator as for instance a light source), which produces a signal with a broad emission spectrum and at least two signal detectors (e.g. optical detectors) with preferably narrow absorption spectrum. Organic light emitting diodes and organic light detectors fulfil these requirements. A single organic light emitting diode (OLED), two organic light detectors, and a plurality of organic transistors can be combined. The OLED can have a wide spectrum, which emits light of a first frequency (e.g., red light) and a second frequency (e.g., different red light or IR light), and for which the emission spectrum is known (see FIG. 8). This figure shows an OLED emission spectrum showing light emission from about 600 nm (yellow) to 800 nm (infrared). Such an approach could be used for weighting the different detected signals as a function of their relative initial strengths. A first detector absorbs light in a first frequency range (e.g., the first light frequency), and a second detector absorbs light in a second frequency range (e.g., the second light frequency). The first and second frequency range can be substantially centred around the first light frequency and the second light frequency, respectively. The detectors can be such that they are mainly absorbing light of the first frequency and the second frequency, respectively. This is illustrated in FIG. 7. It shows the absorption spectra of rather 2 similar molecules, i.e. F16CuPc and NiPc. However, at 600 nm NiPc absorbs substantial more than F16CuPc (about 50% more), whereas at 800 nm F16CuPc absorbs much more than NiPc. In order to avoid interference between detectors, the frequency ranges preferably do not have a substantial overlap region. These embodiments allow the contemporaneous measurements of light of two different frequencies.

For many applications measurements on different locations can be used. An example is measurement of the oxygen content of blood in a tissue. Oxygen content in the blood gives information on the wound healing process or concerning the location of a bacterial infection. In case of wound healing or detecting the location of a bacterial infection, it is useful to measure the oxygen content in the skin at different locations. Instead of scanning one combination of LED, detector, and circuitry over the wound, combinations of LEDs, detectors, circuitry and switching elements, called a sensor unit, can be repeated to cover a larger area, such that parallel measurements over a larger area become possible. The sensors units can be repeated in a one- or a two-dimensional array or in other geometrical configurations. The exact location of the sensor units depends on the topography and shape of surface to be measured. The sensor units with light emitting diodes, light detectors and transistors may be organized in matrix form. Each matrix element of the matrix or else each sensor unit of the sensor can comprise a single or a plurality of organic light emitting diode and a single or a plurality of organic light detector and circuitry comprising a plurality of organic transistors.

Blind detectors may be added in some sensor units of such an array to eliminate dark current. These additional light detectors are covered to prevent incident light from entering. Each matrix element of a matrix may include two different light emitting diodes, two different light detectors and a plurality of transistors. One of the two detectors may be a blind detector (e.g., can be covered in order to prevent light to fall in). Each matrix element of the matrix may include a circuit using the transistors to amplify the signal difference between the two light detectors. In each matrix cell or in a certain set of matrix cells (for instance a row or a column in a matrix) a blind detector can be used. Also two blind light detectors may be added to each matrix cell or may be added to certain rows or columns of the said matrix.

Each matrix element of the matrix may include two different light emitting diodes, four different light detectors and a plurality of transistors. Here, two of the four said light detectors may be covered to prevent incident light from falling in.

Two circuits can then be present per matrix cell which use the transistors to amplify the signal differences between the light detectors.

These arrays can be produced relatively easy and cheaply in organic materials. Plastic components may be deposited by e.g. printing, evaporation or spin-coating and other known preferably low-cost techniques for organic electronics fabrication. Moreover, relatively high integration densities can be achieved and different constituting elements can be processed in parallel, i.e. in the same process steps. This also allows for inexpensive production of one and two dimensional arrays with measurement places each having their signal generator and their signal detector and underlying electronics, providing one or two-dimensional pictures of the characteristics of the material under measurement.

Also, at least one connector for power and signals may be present. Further, a pre-amplification circuit may be included within the device.

Furthermore read-out electronics can be added, meaning specific control structures for the readout of this matrix. A method for reading out the charge on the capacitances of the sensor units includes reading the charges out in a sequential manner to obtain an image of the characteristic. Each sensor unit can correspond to one pixel of the image. A readout circuit can be integrated in the array of sensor units and may be specifically adapted for use with low-cost organic electronics.

A display or possibly a flexible display made of organic material, may be added to provide the images or measurements. The read-out circuitry realises an image of the characteristic on this display.

As mentioned before several times, in many cases it is beneficial to make these detectors, LEDs, and circuitry parts in organic materials. This is especially the case when making a large array of sensor units. These materials are flexible and the sensor or array of sensor units can be applied on materials with different geometry, such as a human body. These materials can be deposited by low-cost techniques for organic electronics fabrication allowing for mass production. Furthermore, different constituting elements can be processed in parallel, i.e. in the same process steps allows for production of one and two dimensional arrays each having their signal generator and their signal detector and underlying electronics. Also, relatively high integration densities can be achieved.

Methods that can be used for depositing organic material are printing, evaporation or spin-coating and other known methods.

Intelligent wound care that allows inspection of wound healing is currently used for different applications. An example is the inspection of the "survival of a flap" after an operation in which a part of the skin has been transplanted. Presence of blood flow indicates that the skin will survive. Another example is inspection of wound infection by detection of (local) increased blood oxygen consumption. Also detection of bedsores and blood flow problems related to diabetics is possible. Different techniques to measure the blood flow through the skin exist, such as duplex US-Doppler echography, IR laser scanning, and NIR reflection spectroscopy. However, the spatial resolution of these techniques is too low. Also opening of the bandage, covering the wound, is required which may impede the healing process. Blood strongly absorbs and scatters red light. The blood pressure goes up and down with the heartbeat and so does (by expansion) the volume of blood in the blood vessels. The scattering and reflection of all other skin tissue remains substantially unchanged with the heartbeat, only the reflection by the blood vessel changes. This has been used before to determine the heartbeat by the global reflection of a large spot. Also a small spot from a glass fiber has been used to determine the blood flow locally. A physician using such a technique has to move the glass fiber over the wound. Taking such measurements requires that the bandage covering a wound be opened, which increases the risk of infection. Further, the oxygen level can be determined if two different light sources are used, due to the difference in scattering and reflection between oxyhemoglobin and hemoglobin.

Other approaches use a classical detector and a classical LED, which are not flexible, but are integrated on a flexible substrate for application on a human or animal body. This technique causes non-uniform pressure on the body, which hampers the measurement accuracy, reduces patient comfort and may negatively impact the healing process.

A sensor comprising an array or matrix of different sensor units made of organic materials as described above allows a uniform pressure on a wound. When made in organic materials high spatial resolution can be obtained. Furthermore monitoring blood flow through the skin without opening the bandage is possible.

Embodiments described above may be integrated in a bandage, which is used to cover and protect wounds. Measuring a characteristic of human or animal tissue or wound of a living human or animal, related to either oxygen or blood flow within the tissue or wound is possible. The method includes performing measurements on at least one place on said tissue, or on a plurality of places, preferably arranged in a one or two dimensional array (which may be denoted as matrix or regular grid pattern). Depending on the embodiment the measurement duration may exceed at least one heart beat cycle, or a plurality of heat beat cycles, such as for example 10, 50, 100, 500, 1,000, 2,000, 5,000, 10,000 or 100,000, heart beat cycles.

The sets of measurement intervals can correspond with specific repetitions in the heartbeat cycle. In such way, an integrated value and subsequent read-out of said integrated value are achieved and the characteristic of the human or animal tissue can be determined from said integrated value.

In situations where OLEDs and corresponding organic detectors of only one colour or frequency are used, the blood flow in the skin under the bandage can be imaged without opening the bandage.

The blood oxygen level in the skin under the bandage can also be imaged when active circuitry for measuring two different wavelengths is used. Therefore organic OLEDs with two different wavelengths in combination with 1 broadband organic detector and a plurality of organic transistors may be used. Otherwise, OLEDs and corresponding organic detectors of two different colours or frequencies can be used, Other characteristics of human or animal tissue which can be measured according to the techniques described herein are for instance linked with the presence or concentration of certain constituents of the blood, or the concentration or presence of markers in the blood, which may have been added to it. In preferred embodiments the presence or concentration has periodic behaviour with a frequency that corresponds to the heartbeat frequency.

In certain embodiments, a control logic block which can determine the occurrence of high and low blood pressure is further included. Such a control logic block may comprise a plurality of capacitances that are charged by one or more signals originating from one, two or more organic light detector(s) on at about the specific times of high or low blood pressure. Some capacitances may be charged at high blood pressure occurrences while others may be charged at low blood pressure occurrences. These capacitances can be charged over different heartbeat periods as described above, such that the signal-to-noise ratio of the image can be improved.

The scattered light from the OLEDs is measured by the organic detectors in conjunction with a heartbeat cycle of a patient to which the bandage is applied. The difference between high blood-pressure low blood-pressure signals is sampled for several periods to average noise effects out. The organic transistors in the circuit control the sampling period, the signal amplification and the read-out selection.

Embodiments described above may be integrated in a bandage, which is used to cover and protect wounds.

Figure 9:
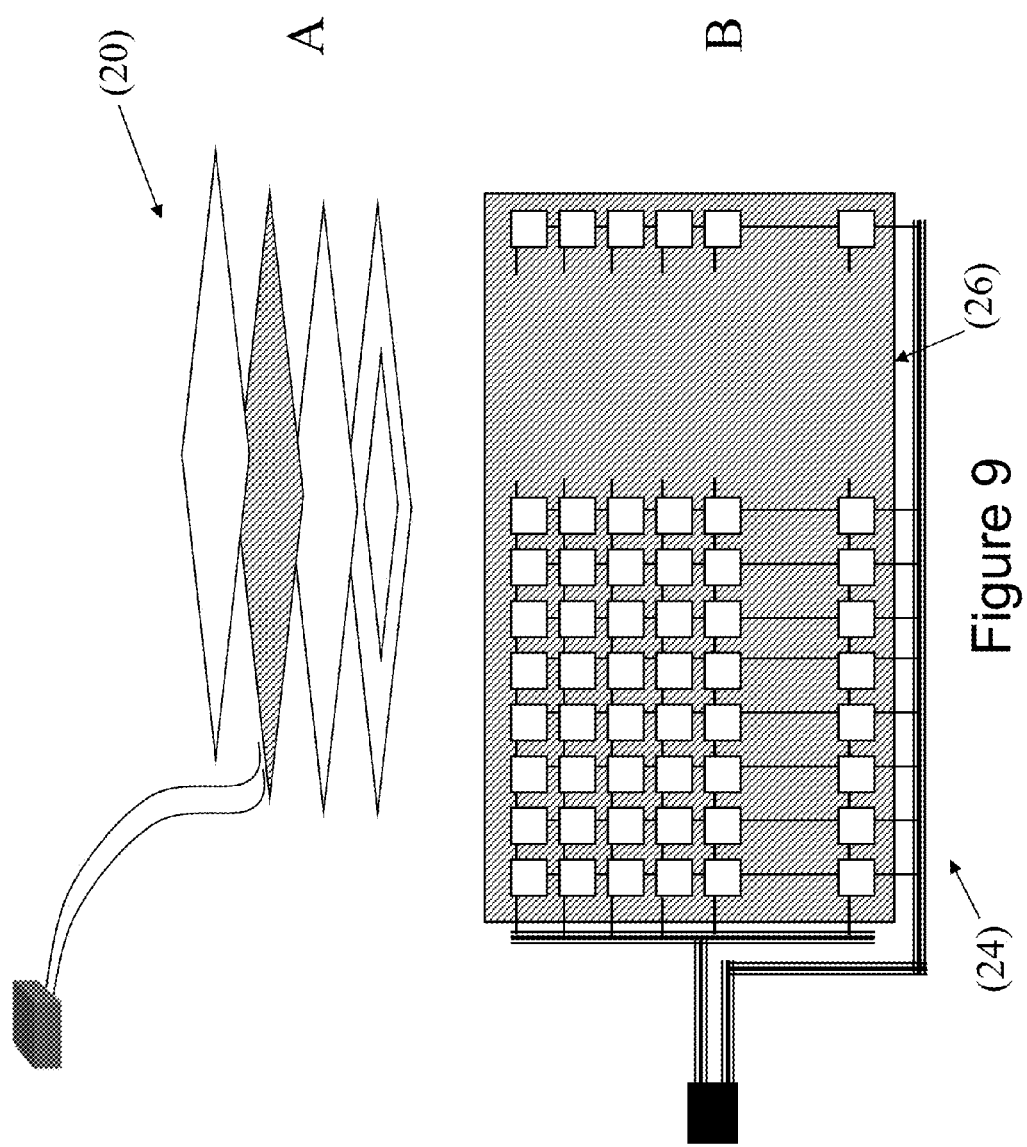
FIG. 9A represents a flexible bandage where the organic electronics layer is incorporated between the adhesive and wound-care layer and the protective top layer of the bandage.
FIG. 9B illustrates a matrix structure of an organic electronics layer and its readout, where each matrix element contains OLED(s), organic detector(s) and a control logic block.

In certain embodiments, a matrix (24) of OLEDs, organic detectors and organic transistors can be integrated on a thin foil (26) (FIG. 9B), preferably a flexible thin foil, that is incorporated into a bandage (20) (see FIG. 9A).

In other embodiments several thin foils may be incorporated in the bandage, each with its own functionality. An example is a combination of foils to implement a blood flow patch, an oximeter patch, a direct read-out, a differential read-out with a blind reference detector in the matrix cell, or in a matrix row, or in a matrix column, or one cell per matrix.

In certain embodiments, if wound liquids are produced, the thin foil(s) on which the OLEDs, organic detectors and organic transistors are disposed may include holes (e.g. round holes, but any shape can be used) or trenches (e.g., rectangular trenches) to allow the wound liquids to be absorbed by other parts of the bandage (e.g., gauze material).

In other embodiments, additional layers may be incorporated for wound healing and wound protection. In certain embodiments a (set of) sealing layer(s) is further included.

In certain implementations, a device in the form of a layer of low-cost plastic electronics is added into a classical disposable bandage that is used to cover a wound, for instance, after an operation or during (emergency) first-aid care. This additional layer allows for a read-out to produce an image containing information about the wound healing process. This is done by connecting external contacts on the bandage to appropriate read-out equipment.

Still further, a mechanism for attaching the above-mentioned device removably to the (human) body is included (such as an adhesive strip).

This measurement method using organic light emitting diodes, organic photo detectors, and organic circuitry may also be included in foils for making colour or grey scale copies of curved or bent surfaces, such as old books. A method and tool for copying black and white pictures of bent surfaces is already known. Using this method with one organic LED and at least one detector also grey scale copies can be made. Using a wideband organic LED and at least three narrow band organic light detectors (for example yellow, blue and red) also colour copies can be made.

The method may also be used to detect the composition of a gas flowing in a tube. In case this is a periodic flow, the measurement can be done without introducing an extra periodical signal. In case the gas flow is continuous, a periodic signal can be obtained by modulating the organic light emitting diode(s).

The invention claimed is:

1. A sensor comprising at least one sensor unit, each sensor unit comprising:
a charge storage element;
a first circuitry part connected between said charge storage element and a first measurement element recording a measurement signal, said first circuitry part being provided for periodically applying a first measurement current indicative of a first recorded measurement value to said charge storage element for charging said charge storage element, said first circuitry part comprising a first switching element;
a second circuitry part connected between said charge storage element and either said first measurement element or a second measurement element recording said measurement signal, said second circuitry part provided for periodically applying a second measurement current indicative of a second recorded measurement value to the charge storage element for discharging said charge storage element, said second measurement current consisting of components to be eliminated from said first measurement current, said second circuitry part comprising a second switching element;
said first and second switching elements being switchable between a conducting state and a non-conducting state;
a third circuitry part connected between said charge storage element and an output of said sensor, said third circuitry part comprising a third switching element switchable between a conducting and a non-conducting state; and
control circuitry for applying voltages to said first and second switching elements according to a predetermined periodic timing scheme, such that in each period of said timing scheme said first and second switching elements are switched to the conducting state for a given time and that the charge stored on said charge storage element as a result of the components to be eliminated from the first measurement current is substantially equal to said charge which is removed from the charge storage element as a result of the second measurement current;
wherein:
said charge storage element and said first, second and third circuitry parts are made of organic materials, each of said switching elements in each sensor unit having an uncertain threshold voltage, said conducting and non-conducting states being located on opposite sides of a predetermined voltage range containing said uncertain threshold voltage;
said control circuitry is adapted for applying voltages to said switching elements outside said predetermined voltage range; and
said third switching element is arranged for conducting charge stored on the charge storage element to said output, said third circuitry part being designed for periodically conducting said charge after a predefined number of said periods.

2. A sensor according to claim 1, wherein said first circuitry part consists of said first switching element, said second circuitry part consists of said second switching element and a current mirror, and said third circuitry part consists of said third switching element.

3. A sensor according to claim 1, wherein said first and second circuitry parts in said sensor units are current sources arranged as a current mirror.

4. A sensor according to claim 1, wherein each sensor unit is adapted for treating a periodic measurement signal, and wherein said timing scheme is determined such that said first measurement value is around the maximum of said periodic signal and said second measurement value is around the minimum of said periodic measurement signal.

5. A sensor according to claim 4, wherein said control circuitry comprises a control logic block to determine the occurrence of said maximum and said minimum.

6. A sensor according to claim 1, wherein for each sensor unit said first measurement element comprises at least one light detector connected to said first and second circuitry parts and wherein said timing scheme is synchronized with a periodic illumination scheme of said at least one light detector.

7. A sensor according to claim 1, wherein said first measurement element comprises a light detector connected to said first circuitry part, and said second measurement element comprises a blind detector connected to said second circuitry part, said blind detector being a light detector covered from incident light.

8. A sensor according to claim 6, wherein each sensor unit further comprises at least one light emitting diode.

9. A sensor according to claim 8, wherein each sensor unit further comprises a light-absorbing or light-reflecting layer between said at least one light emitting diode and said at least one light detector.

10. A sensor according to claim 8, wherein each sensor unit comprises a light emitting diode with a broad emission spectrum, two light detectors with a narrow absorption spectrum, said narrow absorption spectra of said two light detectors being different, said two narrow absorption spectra falling within said broad emission spectrum of said light emitting diode.

11. A sensor according to claim 1, comprising a plurality of sensor units arranged in a one or two dimensional matrix.

12. A sensor according to claim 11, further comprising at least one connector for power and signals.

13. A sensor according to claim 11, further comprising read-out electronics for reading out said sensors in a sequential manner.

14. A sensor according to claim 13, further comprising a display, said read-out electronics being provided for realizing on said display a one or two-dimensional image of said charges on said charge storage elements in said one or two dimensional matrix.

15. A sensor according to claim 10, wherein said light emitting diode is made of organic materials.

16. A sensor according to claim 15, further comprising a flexible material.

17. A sensor according to claim 16, wherein said flexible material is a bandage for covering a wound.

18. A sensor according to claim 16, wherein said flexible material is a foil incorporated in a bandage for covering a wound.

19. A sensor array according to claim 18, wherein said foil comprises a first foil comprising said organic light emitting diodes, a second foil comprising said organic light detectors, and a third foil comprising each of said circuitry parts.

20. A sensor array according to claim 19 wherein said foils include holes or trenches.

* * * * *

UNITED STATES PATENT AND TRADEMARK OFFICE
CERTIFICATE OF CORRECTION

PATENT NO.        : 8,423,105 B2
APPLICATION NO.   : 11/918816
DATED             : April 16, 2013
INVENTOR(S)       : Genoe et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1581 days.

Signed and Sealed this
Eighth Day of September, 2015

Michelle K. Lee
*Director of the United States Patent and Trademark Office*